(12) United States Patent
Longo et al.

(10) Patent No.: US 11,980,555 B2
(45) Date of Patent: *May 14, 2024

(54) IMPLANTABLE STENT

(71) Applicant: Vesper Medical, Inc., Wayne, PA (US)

(72) Inventors: Michael A. Longo, Glenmoore, PA (US); William James Harrison, Signal Mountain, TN (US)

(73) Assignee: VESPER MEDICAL, INC., Wayne, PA (US)

( * ) Notice: Subject to any disclaimer, the term of this patent is extended or adjusted under 35 U.S.C. 154(b) by 16 days.

This patent is subject to a terminal disclaimer.

(21) Appl. No.: 17/733,048

(22) Filed: Apr. 29, 2022

(65) Prior Publication Data
US 2022/0257394 A1    Aug. 18, 2022

Related U.S. Application Data

(63) Continuation of application No. 16/671,859, filed on Nov. 1, 2019, now Pat. No. 11,344,439, which is a
(Continued)

(51) Int. Cl.
| | | |
|---|---|---|
| *A61F 2/915* | (2013.01) | |
| *A61F 2/07* | (2013.01) | |
| *A61F 2/88* | (2006.01) | |

(52) U.S. Cl.
CPC .............. *A61F 2/915* (2013.01); *A61F 2/07* (2013.01); *A61F 2/88* (2013.01); *A61F 2/885* (2013.01);
(Continued)

(58) Field of Classification Search
CPC .... A61F 2/915; A61F 2/07; A61F 2/88; A61F 2/885; A61F 2002/91583; A61F 2250/0036; A61F 2250/0028
See application file for complete search history.

(56) References Cited

U.S. PATENT DOCUMENTS

| | | |
|---|---|---|
| 5,104,404 A | 4/1992 | Wolff |
| 5,449,373 A | 9/1995 | Pinchasik et al. |

(Continued)

FOREIGN PATENT DOCUMENTS

| | | |
|---|---|---|
| EP | 1088528 | 4/2001 |
| EP | 3043754 | 7/2016 |

(Continued)

OTHER PUBLICATIONS

International Search Report and Written Opinion for Application No. PCT/USD2019/021322 dated May 21, 2019.

*Primary Examiner* — Paul B Prebilic

(57) ABSTRACT

Implantable stents that include strips that are each comprised of main struts connected by first connectors, and adjacent strips are connected by second connectors. The strut connectors have a structure, including areas of expanded or reduced width or thickness, to account for venous applications. When used for venous applications, the stents convey benefit from configurations that improve flexibility (due to the greater elasticity of venous applications) while maintaining enough stiffness to resist pressure on the venous structure in selected areas (such as for the May-Thurner syndrome). The stents include particular structural characteristics that are particularly advantageous for (although not limited to) venous applications.

6 Claims, 11 Drawing Sheets

Related U.S. Application Data continuation of application No. 15/916,843, filed on Mar. 9, 2018, now Pat. No. 10,500,078.

(52) U.S. Cl.
CPC .............. *A61F 2002/91583* (2013.01); *A61F 2250/0036* (2013.01)

(56) References Cited

U.S. PATENT DOCUMENTS

| | | |
|---|---|---|
| 5,827,321 A | 10/1998 | Roubin et al. |
| 5,836,966 A | 11/1998 | St. Germain |
| 5,843,120 A | 12/1998 | Israel et al. |
| 5,843,175 A | 12/1998 | Frantzen |
| 5,868,780 A | 2/1999 | Lashinski et al. |
| 5,868,782 A | 2/1999 | Frantzen |
| 5,911,754 A | 6/1999 | Kanesaka et al. |
| 5,922,005 A | 7/1999 | Richter et al. |
| 5,938,697 A | 8/1999 | Killion et al. |
| 5,964,798 A | 10/1999 | Imran |
| 5,972,018 A | 10/1999 | Israel et al. |
| 6,027,526 A | 2/2000 | Limon et al. |
| 6,033,433 A | 3/2000 | Ehr et al. |
| 6,042,606 A | 3/2000 | Frantzen |
| 6,059,811 A | 5/2000 | Pinchasik et al. |
| 6,068,656 A | 5/2000 | Von Oepen |
| 6,083,259 A | 7/2000 | Frantzen |
| 6,106,548 A | 8/2000 | Roubin et al. |
| 6,113,627 A | 9/2000 | Jang |
| 6,123,721 A | 9/2000 | Jang |
| 6,146,403 A | 11/2000 | St. Germain |
| 6,156,052 A | 12/2000 | Richter |
| 6,179,868 B1 | 1/2001 | Burpee et al. |
| 6,183,507 B1 | 2/2001 | Lashinski et al. |
| 6,190,403 B1 | 2/2001 | Fischell et al. |
| 6,200,334 B1 | 3/2001 | Jang |
| 6,203,569 B1 | 3/2001 | Wijay |
| 6,235,053 B1 | 5/2001 | Jang |
| 6,241,762 B1 | 6/2001 | Shanley |
| 6,261,319 B1 | 7/2001 | Kveen et al. |
| 6,287,336 B1 | 9/2001 | Globerman et al. |
| 6,299,635 B1 | 10/2001 | Frantzen |
| 6,309,414 B1 | 10/2001 | Rolando et al. |
| 6,325,821 B1 | 12/2001 | Gaschino et al. |
| 6,325,825 B1 | 12/2001 | Kula et al. |
| 6,402,777 B1 | 6/2002 | Globerman et al. |
| 6,428,570 B1 | 8/2002 | Globerman |
| 6,443,982 B1 | 9/2002 | Israel et al. |
| 6,451,049 B2 | 9/2002 | Vallana et al. |
| 6,461,380 B1 | 10/2002 | Cox |
| 6,461,381 B2 | 10/2002 | Israel et al. |
| 6,464,722 B2 | 10/2002 | Israel et al. |
| 6,475,236 B1 | 11/2002 | Roubin |
| 6,478,816 B2 | 11/2002 | Kveen et al. |
| 6,485,508 B1 | 11/2002 | McGuinness |
| 6,485,509 B2 | 12/2002 | Killion et al. |
| 6,497,723 B1 | 12/2002 | Starck et al. |
| 6,540,775 B1 | 4/2003 | Fischell et al. |
| 6,610,086 B1 | 8/2003 | Kock et al. |
| 6,635,084 B2 | 10/2003 | Israel et al. |
| 6,638,300 B1 | 10/2003 | Frantzen |
| 6,641,609 B2 | 11/2003 | Globerman |
| 6,660,019 B1 | 12/2003 | Richter et al. |
| 6,679,911 B2 | 1/2004 | Burgermeister |
| 6,682,554 B2 | 1/2004 | Oepen et al. |
| 6,692,522 B1 | 2/2004 | Richter |
| 6,699,281 B2 | 3/2004 | Vallana et al. |
| 6,706,061 B1 | 3/2004 | Fischell et al. |
| 6,709,453 B2 | 3/2004 | Pinchasik et al. |
| 6,730,116 B1 | 5/2004 | Wolinsky et al. |
| 6,746,479 B2 | 6/2004 | Her et al. |
| 6,761,731 B2 | 7/2004 | Majercak |
| 6,764,506 B2 | 7/2004 | Roubin et al. |
| 6,786,922 B2 | 9/2004 | Schaeffer |
| 6,790,227 B2 | 9/2004 | Burgermeister |
| 6,818,015 B2 | 11/2004 | Hankh et al. |
| 6,923,829 B2 | 8/2005 | Boyle et al. |
| 6,939,373 B2 | 9/2005 | Gomez et al. |
| 6,945,993 B2 | 9/2005 | Kveen et al. |
| 7,004,968 B2 | 2/2006 | Lootz et al. |
| 7,029,493 B2 | 4/2006 | Majercak et al. |
| 7,037,330 B1 | 5/2006 | Rivelli, Jr. et al. |
| 7,060,088 B1 | 6/2006 | Fischell et al. |
| 7,060,090 B2 | 6/2006 | Thornton |
| 7,070,614 B1 | 7/2006 | Neuss et al. |
| 7,131,993 B2 | 11/2006 | Gregorich |
| 7,141,062 B1 | 11/2006 | Pinchasik et al. |
| 7,273,494 B2 | 9/2007 | Rolando et al. |
| 7,316,710 B1 | 1/2008 | Cheng et al. |
| 7,326,243 B2 | 2/2008 | Kveen et al. |
| 7,344,563 B2 | 3/2008 | Vallana et al. |
| 7,357,813 B2 | 4/2008 | Burgermeister |
| 7,402,169 B2 | 7/2008 | Killion |
| 7,485,130 B2 | 2/2009 | St. Germain |
| 7,527,644 B2 | 5/2009 | Mangiardi et al. |
| 7,621,947 B2 | 11/2009 | Richter et al. |
| 7,648,526 B2 | 1/2010 | Sano et al. |
| 7,686,843 B2 | 3/2010 | Moore |
| 7,731,746 B2 | 6/2010 | Kveen et al. |
| 7,806,918 B2 | 10/2010 | Nissl et al. |
| 7,862,607 B2 | 1/2011 | McDermott et al. |
| 7,896,912 B2 | 3/2011 | Shanley |
| 8,012,196 B2 | 9/2011 | Smith et al. |
| 8,016,874 B2 | 9/2011 | Casey |
| 8,128,679 B2 | 3/2012 | Casey |
| 8,206,427 B1 | 6/2012 | Ryan et al. |
| 8,211,163 B2 | 7/2012 | Dakin |
| 8,221,489 B2 | 7/2012 | Issenmann et al. |
| 8,257,424 B2 | 9/2012 | Orlowski |
| 8,267,991 B2 | 9/2012 | De Scheerder et al. |
| 8,317,854 B1 | 11/2012 | Ryan et al. |
| 8,317,859 B2 | 11/2012 | Snow et al. |
| 8,337,544 B2 | 12/2012 | Osman et al. |
| 8,348,990 B2 | 1/2013 | Boyle et al. |
| 8,470,021 B2 | 6/2013 | Magnuson et al. |
| 8,524,132 B2 | 9/2013 | Von Oepen et al. |
| 8,562,665 B2 | 10/2013 | Jang |
| 8,647,379 B2 | 2/2014 | McDermott et al. |
| 8,652,196 B2 | 2/2014 | Nissl |
| 8,668,731 B2 | 3/2014 | Kveen et al. |
| 8,888,837 B2 | 11/2014 | Obradoviċet al. |
| 8,974,514 B2 | 3/2015 | Anukhin et al. |
| 9,066,825 B2 | 6/2015 | Chanduszko |
| 9,271,852 B2 | 3/2016 | Bressloff |
| 9,320,627 B2 | 4/2016 | Casey |
| 9,375,810 B2 | 6/2016 | Mangiardi |
| 9,408,727 B2 | 8/2016 | Ainsworth et al. |
| 9,445,926 B2 | 9/2016 | Jang |
| 9,498,360 B2 | 11/2016 | Layman et al. |
| 9,554,927 B2 | 1/2017 | Bales, Jr. et al. |
| 9,561,123 B2 | 2/2017 | Bales, Jr. et al. |
| 9,622,850 B2 | 4/2017 | Bebb |
| 9,649,211 B2 | 5/2017 | Bonsignore et al. |
| 9,655,998 B2 | 5/2017 | Gemborys |
| 9,668,895 B2 | 6/2017 | Dreher |
| 9,668,898 B2 | 6/2017 | Wong |
| 9,693,860 B2 | 7/2017 | Sandstrom et al. |
| 9,700,448 B2 | 7/2017 | Snow et al. |
| 9,707,110 B2 | 7/2017 | McDermott et al. |
| 9,724,220 B2 | 8/2017 | Rasmussen |
| 9,770,348 B2 | 9/2017 | Wack |
| 9,795,496 B2 | 10/2017 | Armstrong et al. |
| 9,839,538 B2 | 12/2017 | Grewe et al. |
| 9,839,540 B2 | 12/2017 | Armstrong et al. |
| 10,076,431 B2 | 9/2018 | Sirhan et al. |
| 2001/0014822 A1 | 8/2001 | Milo |
| 2001/0044649 A1 | 11/2001 | Vallana |
| 2001/0047200 A1 | 11/2001 | White et al. |
| 2002/0013616 A1 | 1/2002 | Carter et al. |
| 2002/0042648 A1 | 4/2002 | Schaldach et al. |
| 2002/0058990 A1 | 5/2002 | Jang |
| 2002/0120327 A1 | 8/2002 | Cox et al. |
| 2003/0009214 A1 | 1/2003 | Shanley |
| 2003/0014102 A1 | 1/2003 | Hong et al. |

(56) References Cited

U.S. PATENT DOCUMENTS

| | | |
|---|---|---|
| 2003/0055485 A1 | 3/2003 | Lee et al. |
| 2003/0100941 A1 | 5/2003 | Fischell et al. |
| 2003/0105513 A1 | 6/2003 | Moriuchi et al. |
| 2003/0105517 A1 | 6/2003 | White et al. |
| 2004/0054398 A1 | 3/2004 | Cully et al. |
| 2004/0054400 A1 | 3/2004 | Granada |
| 2004/0102835 A1 | 5/2004 | Israel et al. |
| 2004/0133265 A1 | 7/2004 | Duffy |
| 2004/0254627 A1 | 12/2004 | Thompson et al. |
| 2004/0267350 A1 | 12/2004 | Roubin et al. |
| 2005/0004657 A1 | 1/2005 | Burgermeister |
| 2005/0021130 A1 | 1/2005 | Kveen et al. |
| 2005/0060024 A1 | 3/2005 | Lee et al. |
| 2005/0080479 A1 | 4/2005 | Feng et al. |
| 2006/0025852 A1 | 2/2006 | Armstrong et al. |
| 2006/0129227 A1 | 6/2006 | Hengelmolen |
| 2006/0173531 A1 | 6/2006 | Richter |
| 2007/0005126 A1 | 1/2007 | Tischler |
| 2007/0010869 A1 | 1/2007 | Sano |
| 2007/0213806 A1 | 9/2007 | Roubin et al. |
| 2007/0213807 A1 | 9/2007 | Roubin et al. |
| 2007/0219613 A1 | 9/2007 | Kao et al. |
| 2007/0239251 A1 | 10/2007 | Prabhu et al. |
| 2008/0009938 A1 | 1/2008 | Huang et al. |
| 2008/0051878 A1 | 2/2008 | Cheng et al. |
| 2008/0140181 A1 | 6/2008 | Reynolds et al. |
| 2008/0177373 A1 | 7/2008 | Huang et al. |
| 2008/0288048 A1 | 11/2008 | Rolando et al. |
| 2008/0300674 A1 | 12/2008 | Jang |
| 2009/0018641 A1 | 1/2009 | Binkert |
| 2009/0062899 A1 | 3/2009 | Dang et al. |
| 2010/0004736 A1 | 1/2010 | Rolando et al. |
| 2010/0222864 A1 | 9/2010 | Rivelli, Jr. et al. |
| 2010/0241216 A1 | 9/2010 | Rolando et al. |
| 2011/0125251 A1 | 2/2011 | Cottone et al. |
| 2011/0106237 A1 | 5/2011 | Bonsignore et al. |
| 2011/0230957 A1 | 9/2011 | Bonsignore et al. |
| 2012/0043703 A1 | 2/2012 | Von Oepen et al. |
| 2012/0046729 A1 | 2/2012 | Von Oepen et al. |
| 2012/0046730 A1 | 2/2012 | Von Oepen et al. |
| 2012/0046731 A1 | 2/2012 | Von Oepen et al. |
| 2012/0046733 A1 | 2/2012 | Von Oepen et al. |
| 2012/0046739 A1 | 2/2012 | Von Oepen et al. |
| 2012/0143312 A1 | 6/2012 | Brown |
| 2012/0277844 A1 | 11/2012 | Wu |
| 2012/0310327 A1 | 12/2012 | McHugo |
| 2013/0178928 A1 | 7/2013 | Vyas et al. |
| 2013/0218254 A1 | 8/2013 | Cattaneo et al. |
| 2013/0304192 A1 | 11/2013 | Chanduszko |
| 2013/0325141 A1 | 12/2013 | Gill et al. |
| 2014/0081371 A1 | 3/2014 | Poehlmann et al. |
| 2014/0277365 A1 | 9/2014 | Gillespie |
| 2014/0277378 A1 | 9/2014 | Lane et al. |
| 2015/0105852 A1 | 4/2015 | Noffke et al. |
| 2015/0209167 A1 | 7/2015 | Mangiardi |
| 2015/0250580 A1 | 9/2015 | Besselink |
| 2016/0235562 A1 | 8/2016 | Casey |
| 2016/0250052 A1 | 9/2016 | Kaspar |
| 2016/0287418 A1 | 10/2016 | Cheng et al. |
| 2017/0035548 A1 | 2/2017 | Bebb et al. |
| 2017/0071768 A1 | 3/2017 | Krieger et al. |
| 2017/0086994 A1 | 3/2017 | Bales et al. |
| 2017/0100267 A1 | 4/2017 | Bales et al. |
| 2017/0224878 A1 | 8/2017 | Gemborys |
| 2017/0265998 A1 | 9/2017 | Sandstrom et al. |
| 2017/0281375 A1 | 10/2017 | Longo |
| 2017/0312104 A1 | 11/2017 | McDermott et al. |
| 2017/0312105 A1 | 11/2017 | McDermott et al. |
| 2017/0340464 A1 | 11/2017 | Kovach et al. |
| 2019/0060052 A1 * | 2/2019 | Harrison ............... A61F 2/9522 |
| 2022/0257394 A1 * | 8/2022 | Longo ..................... A61F 2/885 |

FOREIGN PATENT DOCUMENTS

| | | | |
|---|---|---|---|
| EP | 3123983 | 2/2017 | |
| EP | 3284445 A1 * | 2/2018 | ............... A61F 2/82 |
| WO | 2006026779 | 3/2006 | |
| WO | 2009012417 | 1/2009 | |
| WO | 2015038790 | 3/2015 | |
| WO | WO-2016186262 A1 * | 11/2016 | ............... A61F 2/82 |

* cited by examiner

IMPLANTABLE STENT

CROSS-REFERENCE TO RELATED APPLICATIONS

This application is a continuation of U.S. patent application Ser. No. 16/671,859, filed Nov. 1, 2019, now U.S. Pat. No. 11,344,439, which is a continuation of U.S. patent application Ser. No. 15/916,843, filed Mar. 9, 2018, now U.S. Pat. No. 10,500,078, each of which is hereby incorporated by reference in its entirety.

BACKGROUND

Field of the Invention

Disclosed herein are stents for implantation within the body and methods for delivery and/or deployment. Certain embodiments disclosed herein may be used in procedures to treat May-Thurner syndrome and/or deep venous thrombosis and the resulting post-thrombotic syndrome.

Description of the Related Art

May-Thurner syndrome, also known as iliac vein compression syndrome, is a condition in which compression of the common venous outflow tract of the left lower extremity may cause various adverse effects, including, but not limited to, discomfort, swelling, pain, and/or deep venous thrombosis (DVT) (commonly known as blood clots). May-Thurner syndrome occurs when the left common iliac vein is compressed by the overlying right common iliac artery, leading to stasis of blood, which may cause the formation of blood clots in some individuals. Other, less common, variations of May-Thurner syndrome have been described, such as compression of the right common iliac vein by the right common iliac artery.

While May-Thurner syndrome is thought to represent between two to five percent of lower-extremity venous disorders, it frequently goes unrecognized. Nevertheless, it is generally accepted that May-Thurner syndrome is about three times more common in women than it is in men and typically manifests itself between the age of twenty and forty. Patients exhibiting both hypercoagulability and left lower extremity thrombosis may be suffering from May-Thurner syndrome. To confirm that diagnosis, it may be necessary to rule out other causes for hypercoagulable state, for example by evaluating levels of antithrombin, protein C, protein S, factor V Leiden, and prothrombin G20210A.

By contrast to the right common iliac vein, which ascends almost vertically parallel to the inferior vena cava, the left common iliac vein takes a more transverse course. Along this course, it lies under the right common iliac artery, which may compress it against the lumbar spine. Iliac vein compression is a frequent anatomic variant—it is thought that as much as 50% luminal compression of the left iliac vein occurs in a quarter of healthy individuals. However, compression of the left common iliac vein becomes clinically significant only if such compression causes appreciable hemodynamic changes in venous flow or venous pressure, or if it leads to acute or chronic deep venous thrombosis, which will be discussed in more detail below. In addition to the other problems associated with compression, the vein may also develop intraluminal fibrous spurs from the effects of the chronic pulsatile compressive force from the overlying artery.

The narrowed, turbulent channel associated with May-Thurner syndrome may predispose the afflicted patient to thrombosis. And, the compromised blood flow often causes collateral blood vessels to form—most often horizontal transpelvis collaterals, connecting both internal iliac veins to create additional outflow possibilities through the right common iliac vein. Sometimes vertical collaterals are formed, most often paralumbar, which can cause neurological symptoms, like tingling and numbness.

Current best practices for the treatment and/or management of May-Thurner syndrome is proportional to the severity of the clinical presentation. Leg swelling and pain is best evaluated by vascular specialists, such as vascular surgeons, interventional cardiologists, and interventional radiologists, who both diagnose and treat arterial and venous diseases to ensure that the cause of the extremity pain is evaluated. Diagnosis of May-Thurner syndrome is generally confirmed one or more imaging modalities that may include magnetic resonance venography, and venogram, which, because the collapsed/flattened left common iliac may not be visible or noticed using conventional venography, are usually confirmed with intravascular ultrasound. To prevent prolonged swelling or pain as downstream consequences of the left common iliac hemostasis, blood flow out of the leg should be improved/increased. Early-stage or uncomplicated cases may be managed simply with compression stockings. Late-stage or severe May-Thurner syndrome may require thrombolysis if there is a recent onset of thrombosis, followed by angioplasty and stenting of the iliac vein after confirming the diagnosis with a venogram or an intravascular ultrasound. A stent may be used to support the area from further compression following angioplasty. However, currently available stenting options suffer from several complications—including severe foreshortening, lack of flexibility (which can force the vessel to straighten excessively), vessel wear and eventual perforation, increased load on and deformation of the stent causing early fatigue failure, and/or impedance of flow in the overlying left iliac artery potentially causing peripheral arterial disease. The compressed, narrowed outflow channel present in May-Thurner syndrome may cause stasis of the blood, which an important contributing factor to deep vein thrombosis.

Some patients suffering from May-Thurner syndrome may exhibit thrombosis while others may not. Nevertheless, those patients that do not experience thrombotic symptoms may still experience thrombosis at any time. If a patient has extensive thrombosis, pharmacologic and/or mechanical (i.e., pharmacomechanical) thrombectomy may be necessary. The hemostasis caused by May-Thurner syndrome has been positively linked to an increased incidence of deep vein thrombosis ("DVT").

Deep vein thrombosis, or deep venous thrombosis, is the formation of a blood clot (thrombus) within a deep vein, predominantly in the legs. The right and left common iliac are common locations for deep vein thrombosis, but other locations of occurrence are common. Non-specific symptoms associated with the condition may include pain, swelling, redness, warmness, and engorged superficial veins. Pulmonary embolism, a potentially life-threatening complication of deep vein thrombosis, is caused by the detachment of a partial or complete thrombus that travels to the lungs. Post-thrombotic syndrome, another long-term complication associated with deep venous thrombosis, is a medical condition caused by a reduction in the return of venous blood to the heart and can include the symptoms of chronic leg pain, swelling, redness, and ulcers or sores.

Deep vein thrombosis formation typically begins inside the valves of the calf veins, where the blood is relatively oxygen deprived, which activates certain biochemical pathways. Several medical conditions increase the risk for deep vein thrombosis, including cancer, trauma, and antiphospholipid syndrome. Other risk factors include older age, surgery, immobilization (e.g., as experienced with bed rest, orthopedic casts, and sitting on long flights), combined oral contraceptives, pregnancy, the postnatal period, and genetic factors. Those genetic factors include deficiencies with antithrombin, protein C, and protein S, the mutation of Factor V Leiden, and the property of having a non-O blood type. The rate of new cases of deep vein thrombosis increases dramatically from childhood to old age; in adulthood, about 1 in 1000 adults develops the condition annually.

Common symptoms of deep vein thrombosis include pain or tenderness, swelling, warmth, redness or discoloration, and distention of surface veins, although about half of those with the condition have no symptoms. Signs and symptoms alone are not sufficiently sensitive or specific to make a diagnosis, but when considered in conjunction with known risk factors can help determine the likelihood of deep vein thrombosis. Deep vein thrombosis is frequently ruled out as a diagnosis after patient evaluation: the suspected symptoms are more often due to other, unrelated causes, such as cellulitis, Baker's cyst, musculoskeletal injury, or lymphedema. Other differential diagnoses include hematoma, tumors, venous or arterial aneurysms, and connective tissue disorders.

Anticoagulation, which prevents further coagulation but does not act directly on existing clots, is the standard treatment for deep vein thrombosis. Other, potentially adjunct, therapies/treatments may include compression stockings, selective movement and/or stretching, inferior vena cava filters, thrombolysis, and thrombectomy.

In any case, treatment of various venous maladies, including those described above, can be improved with stents. Improvements in stents for venous use are therefore desired.

BRIEF SUMMARY OF THE INVENTION

Accordingly, the present invention in accordance with various embodiments is directed to an implantable intravascular stent for deployment that obviates one or more of the problems due to limitations and disadvantages of the related art.

Disclosed herein are expandable stents that include pluralities of main struts and connector struts. The inventors have designed the struts of and flexible connectors with structure, including areas of expanded or reduced width or thickness, to account for venous applications. As another example, the inventors have recognized that venous applications benefit from configurations that improve flexibility (due to the greater elasticity of venous applications) while maintaining enough stiffness to resist pressure on the venous structure in selected areas (such as for the May-Thurner syndrome).

Stent embodiments below address the above-described needs and confer other advantages by providing a stent structure that reduces foreshortening while providing radial stiffness and flexibility particularly well suited for venous (and similar) applications. Such improvements are, for example, provided by use of oblique (or helically) oriented stent struts with opposingly oriented oblique connectors that form strips or strip fragments. Those strips or strip fragments (or portions) are then interconnected with flexible connectors that further reduce/minimize shortening.

In one embodiment, a stent includes at least one strip including a plurality of main struts and a plurality of first connector struts. The main struts are obliquely oriented to a longitudinal axis of the stent and extend circumferentially around the longitudinal axis of the stent. The first connector struts extend between and connect circumferentially adjacent pairs of the main struts. The stent also includes a plurality of second connector struts extending between and connecting adjacent strip portions. Ends of the second connector struts are connected to the main struts between ends of the main struts so as to reduce foreshortening of the stent during expansion.

In one aspect, the at least one strip is formed into a generally tubular structure. In another aspect, the ends of the main struts define edges of the at least one strip. In another aspect, the main struts are generally straight. In another aspect, the main struts have a width that is at least twice the width of the first connector struts. In another aspect, the main struts of the at least one strip are each oriented at the same oblique angle to the longitudinal axis of the stent.

In another aspect, the main struts of the at least one strip are each oriented at the same oblique angle to the longitudinal axis of the stent and the oblique angle is between 10 to 50 degrees from the longitudinal axis of the stent. In another aspect, the main struts are longer than the first connector struts. In another aspect, the length of each first connector strut is 30%, 50%, or 70% of the length of each main strut.

In another aspect, at least a pair of first connector struts connects each pair of the main struts. In another aspect, an end of one of the pair of first connector struts is connected to an end of one of the pair of the main struts. In another aspect, an end of the second one of the pair of the first connector struts is connected to the opposite end of the other of the pair of main struts.

In another aspect, the first connector struts are obliquely oriented to the longitudinal axis of the stent. In another aspect, the first connector struts are all oriented at the same oblique angle to the longitudinal axis of the stent. In another aspect, the first connector struts are oriented generally opposite the main struts.

In another aspect, each of the first connector struts is generally straight between its ends. In another aspect, the ends of the second connector struts are attached to a middle portion of the main struts. In another aspect, each of the second connector struts has at least one bend. In another aspect, each of the second connector struts has two bends curving in generally opposite directions. In another aspect, the second connector struts attach to a side of the main struts opposite another side of the main struts to which the first connector struts are attached.

In another embodiment, a stent includes at least one strip extending helically around a longitudinal axis of the stent. The at least one strip includes a plurality of main struts and a plurality of first connector struts. The main struts are obliquely oriented to a longitudinal axis of the stent and extend helically around the longitudinal axis of the stent, and the first connector struts extend between and connect circumferentially adjacent pairs of the main struts. The stent also includes a plurality of second connector struts extending between and connecting adjacent strip portions. Ends of the second connector struts are connected to the main struts between ends of the main struts so as to reduce foreshortening of the stent during expansion.

In one aspect, the second connector struts connect adjacent main struts between a middle portion of one main strut to the middle portion of a respective adjacent main strut. In another aspect, each of the second connector struts has at least one bend. In another aspect, each of the second connector struts has at least two bends curving in generally opposite directions.

In another aspect, the first connector struts are obliquely oriented to the longitudinal axis of the stent. In another aspect, the first connector struts are obliquely oriented to the longitudinal axis in a direction that is generally opposite the oblique orientation of the main struts. In another aspect, the main struts are generally straight. In another aspect, the main struts have a width that is at least twice the width of the first connector struts.

In another aspect, the main struts of the at least one strip are each oriented at the same oblique angle to the longitudinal axis of the stent. In another aspect, the main struts of the at least one strip are each oriented at the same oblique angle to the longitudinal axis of the stent and the oblique angle is between 10 to 50 degrees from the longitudinal axis of the stent. In another aspect, the main struts are longer than the first connector struts. In another aspect, the length of each first connector strut is 30%, 50%, or 70% of the length of each main strut.

In another aspect, at least a pair of first connector struts connects each pair of the main struts. In another aspect, an end of one of the pair of first connector struts is connected to an end of one of the pair of the main struts. In another aspect, an end of another one of the pair of the first connector struts is connected to an end of another one of the pair of main struts. In another aspect, each of the first connector struts is generally straight between its ends.

In another embodiment, a stent includes at least two strips including a plurality of main struts and a plurality of first connector struts. The main struts are obliquely oriented to a longitudinal axis of the stent and extend circumferentially around the longitudinal axis of the stent. The first connector struts extend between and connect circumferentially adjacent pairs of the main struts, and the at least two strips form at least two respective circumferential rings. The stent also includes a plurality of second connector struts extending between and connecting adjacent circumferential rings. Ends of the second connector struts are connected to the main struts between ends of the main struts so as to reduce foreshortening of the stent during expansion.

In one aspect, the at least two circumferential rings extend serially along the longitudinal axis of the stent. In another aspect, each respective main strut has an oblique orientation to the longitudinal axis of the stent that is generally opposite the oblique orientation of a respective main strut of an adjacent strip. In another aspect, the first connector struts of each of the at least two strips have an oblique orientation to the longitudinal axis of the stent that is generally opposite the oblique orientation of the first connector struts of an adjacent strip of the at least two strips.

In another aspect, the ends of the main struts define edges of each of the at least two strips. In another aspect, the main struts are generally straight. In another aspect, the main struts have a width that is at least twice the width of the first connector struts. In another aspect, the main struts of the at least two strips are each oriented at the same oblique angle to the longitudinal axis of the stent. In another aspect, the main struts of the at least two strips are each oriented at the same oblique angle to the longitudinal axis of the stent and the oblique angle is between 10 to 50 degrees from the longitudinal axis of the stent.

In another aspect, the main struts are longer than the first connector struts. In another aspect, the length of each first connector strut is 30%, 50%, or 70% of the length of each main strut. In another aspect, at least a pair of first connector struts connects each pair of the main struts. In another aspect, an end of one of the pair of first connector struts is connected to an end of one of the pair of the main struts. In another aspect, an end of another one of the pair of the first connector struts is connected to an end of another one of the pair of main struts.

In another aspect, the first connector struts are obliquely oriented to the longitudinal axis of the stent. In another aspect, the first connector struts of each strip are all oriented at the same oblique angle to the longitudinal axis of the stent. In another aspect, the first connector struts are oriented generally opposite the main struts.

In another aspect, each of the first connector struts is generally straight between its ends. In another aspect, the ends of the second connector struts are attached to a middle portion of the main struts. In another aspect, the second connector struts have an arc shape extending over a space between adjacent circumferential rings.

Further embodiments, features, and advantages of the intravascular stent, as well as the structure and operation of the various embodiments of the intravascular stent, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate an intravascular stent. Together with the description, the figures further serve to explain the principles of the intravascular stent described herein and thereby enable a person skilled in the pertinent art to make and use the intravascular stent.

DETAILED DESCRIPTION

The inventors have observed certain problems in the prior art associated with foreshortening of stents, and in particular foreshortening of stents used for venous applications. Foreshortening causes difficulty in accurately placing the stent in the patient's lumen, since the end which exits the delivery system first will either move the lumen or move in the lumen, toward the constrained end during the deployment. Additionally, this movement can cause trauma to the already compromised/fragile lumen being treated.

Accurate placement is ideal in all medical interventions, but it is vital in areas where the end that is first deployed is critical. Such areas include at vessel bifurcations and branch vessels, so that the implant does not enter or interfere with the portion of the vessel that does not require treatment. Such a bifurcation is present at the inferior vena cava where it branches into right and left iliac veins, as described in more detail below.

Figure 1:
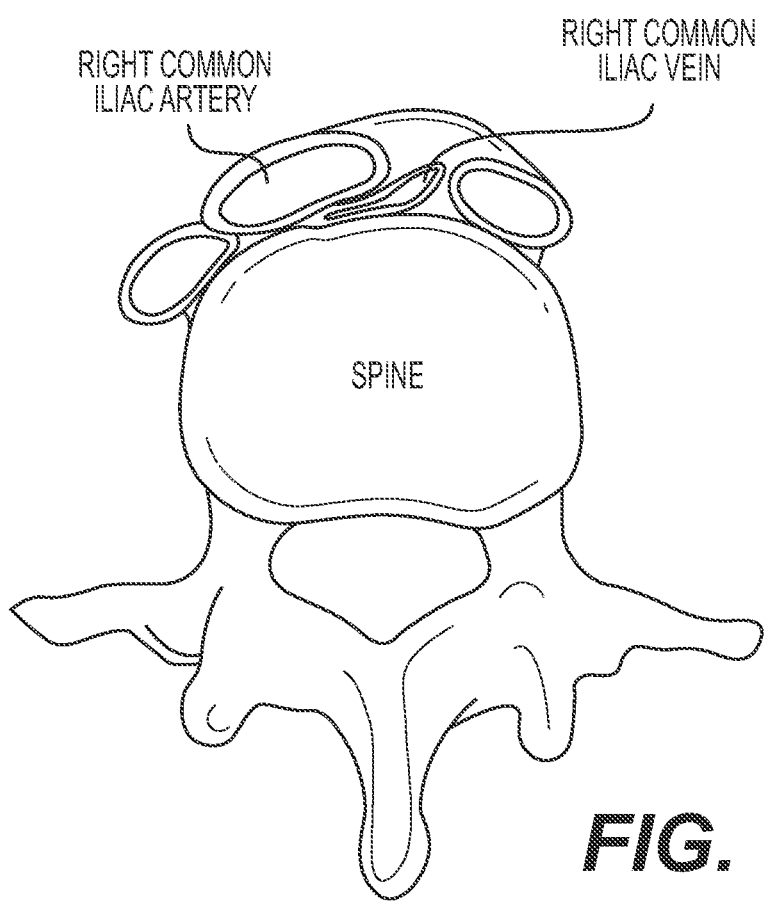
FIG. 1 shows an inferior-posterior view of the L5 lumbar and the bifurcations of the abdominal aorta and inferior vena cava.

May-Thurner syndrome, or iliac vein compression syndrome, occurs in the peripheral venous system when the iliac artery compresses the iliac vein against the spine as shown in FIG. 1. FIG. 1 illustrates a vertebra, the right and left common iliac arteries near the bifurcation of the abdominal aorta, and the right and left common iliac arteries near the bifurcation of the inferior vena cava. The bifurcations generally occur near the L5 lumbar vertebra. Thus, it can be seen that FIG. 1 shows an inferior-posterior view of the L5 lumbar and the bifurcations of the abdominal aorta and inferior vena cava.

As shown, the strong right common iliac artery has compressed the iliac vein causing it to become narrowed. This is one possible, if not a classic, manifestation of May-Thurner syndrome. Over time, such narrowing may cause vascular scarring which can result in intraluminal changes that could precipitate iliofemoral venous outflow obstruction and/or deep vein thrombosis. As discussed above, venous insufficiency (i.e., a condition in which the flow of blood through the veins is impaired) can ultimately lead to various deleterious pathologies including, but not limited to, pain, swelling, edema, skin changes, and ulcerations. Venous insufficiency is typically brought on by venous hypertension that develops as a result of persistent venous obstruction and incompetent (or subcompetent) venous valves. Current treatments for venous outflow obstruction include anticoagulation, thrombolysis, balloon angioplasty and stenting.

Figure 2:
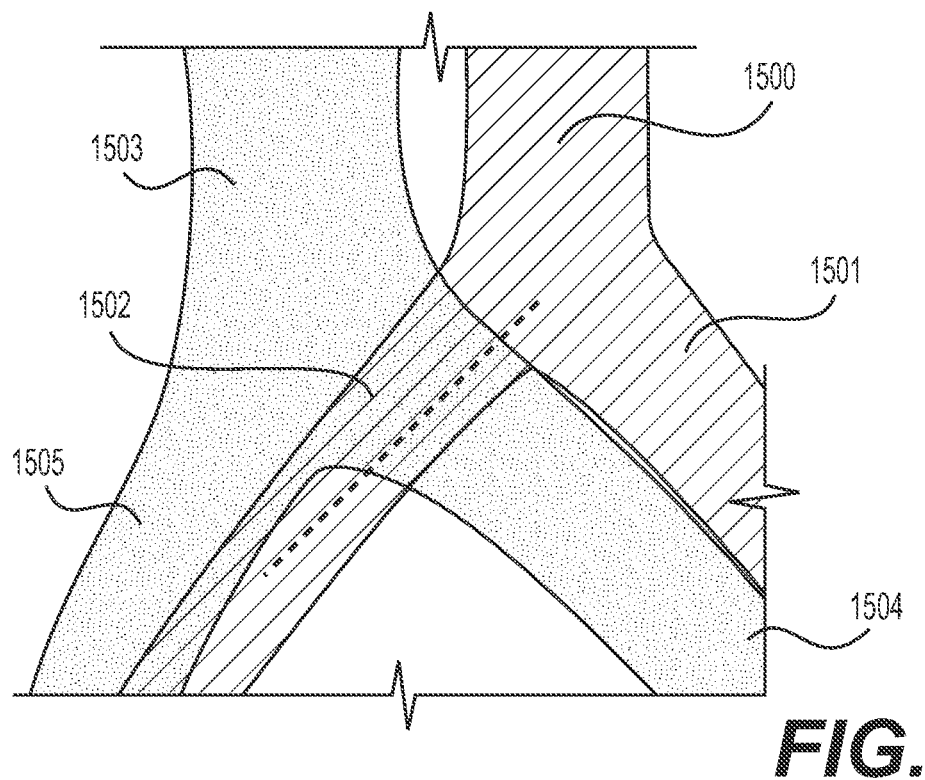
FIG. 2 shows a schematic of the standard overlap of the right common iliac artery over the left common iliac vein.

FIG. 2 illustrates the standard overlap of the right common iliac artery over the left common iliac vein. The arteries shown include the abdominal aorta 1500 branching into the left common iliac artery 1501 and the right common iliac artery 1502. The veins shown include the inferior vena cava 1503 branching into the left common iliac vein 1504 and right common iliac vein 1505. It will be understood that the rough diagram illustrated in FIG. 2 represents the view looking down on a patient laying face-up (i.e., an anterior-poster view of the patient at the location of the bifurcation of the abdominal aorta 1500 and the inferior vena cava 1503). The overlap of the right common iliac artery 1502, which is relatively strong and muscular, over the left common iliac vein 1504 can cause May-Thurner syndrome by pressing down on the vein 1504, crushing it against the spine, restricting flow, and, eventually, causing thrombosis and potentially partially or completely clotting off of the left common iliac vein 1054 and everything upstream of it (i.e., the venous system in the left leg, among others).

Figure 3:
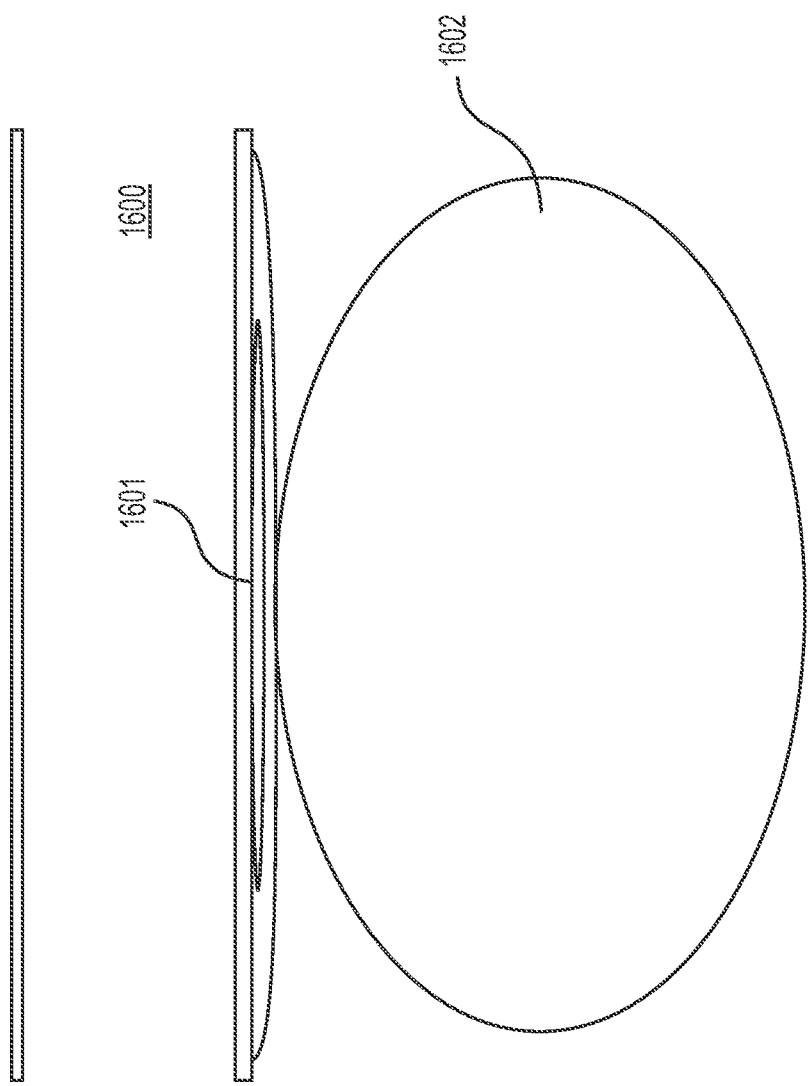
FIG. 3 shows a cross-sectional schematic of the arteriovenous system shown in FIG. 2 taken along the dotted line.

FIG. 3 illustrates a cross-section of the arterio-venous system shown in FIG. 2 taken along the dotted line. Shown in schematic are the right common iliac artery 1600, the left common iliac vein 1601, and a vertebra 1602 of the spine (possibly the L5 lumbar vertebra of the lumbar spine). As can be seen, the right common iliac artery 1600 is substantially cylindrical, due to its strong, muscular construction (among other potential factors). That strong, muscular artery has pressed down on the left common iliac vein 1601, until it has almost completely lost patency, i.e., it is nearly completely pinched off. It will be understood that May-Thurner syndrome may indeed involve such severe pinching/crushing of the underlying left common iliac vein 1601 against the vertebra 1602 of the lumbar spine. However, it will also be understood that May-Thurner syndrome may involve much less pinching/crushing of the underlying left common iliac vein 1601 against the vertebra 1602. Indeed, embodiments disclosed herein are appropriate for the treatment of various degrees of May-Thurner syndrome, including full crushing/pinching of the left common iliac vein 1602 by the right common iliac artery 1600. Other embodiments disclosed herein are appropriate for the treatment of various degrees of May-Thurner syndrome, including, but not limited to a crush/pinch of the underlying left common iliac vein 1601 of between about 10-95%, about 15-90%, about 20-85%, about 25-80%, about 30-75%, about 35-70%, about 40-65%, about 45-60%, and about 50-55%, or any other crush/pinch that could merit treatment using one or more of the devices disclosed herein.

Disclosed herein in accordance with various embodiments are stents that include pluralities of main struts and connector struts. For example, the inventors have designed the struts with structure, including areas of expanded or reduced width or thickness, to account for venous applications. As another example, the inventors have recognized that venous applications benefit from configurations that improve flexibility (due to the greater elasticity of venous applications) while maintaining enough stiffness to resist pressure on the venous structure in selected areas (such as for the May-Thurner syndrome). To that end, explored herein are particular structural characteristics—often expressed as ratios or ranges between different measurements—that the inventors have determined are particularly advantageous for (although not limited to) venous applications.

The dimensions and orientation of these struts are designed to provide flexibility and radial stiffness in combination with substantially reduced or, for practical purposes in venous applications, "zero" foreshortening that is particularly advantageous for use in venous applications. Such advantages are provided by use of oblique (or helically) oriented stent struts with opposingly oriented oblique connectors that form strips or strip fragments. Those strips or strip fragments (or portions) are then interconnected with flexible connectors that further mediate shortening.

Notably the stents herein are not necessarily limited to venous applications unless specifically required by the claims. The disclosed stents could be employed in arterial and biliary applications, for example. But, are particularly suited for the demands of relatively soft structures defining lumens that are subject to much greater bending, twisting, stretching and other contortions and loads than are general atrial lumens.

It should be noted that terms such as "perpendicular", "oblique", "thickness", "length", "width", "adjacent", "middle", and other dimensional and geometric terms should not be regarded as strict or perfect in their application. Instead, geometric and other dimensional reference terms should be interpreted based on their correspondence to accepted manufacturing tolerances and functional needs of the stent on which they are employed. For example, the terms "perpendicular" and "straight" should be appreciated as affording a reasonable amount of angular variation due to manufacturing imperfections or the actual intentional curves cut or formed in the stent design. Also, any thickness, width or other dimension should be assessed based on tolerances and functional needs of the design rather than idealized measurements.

Figure 4:
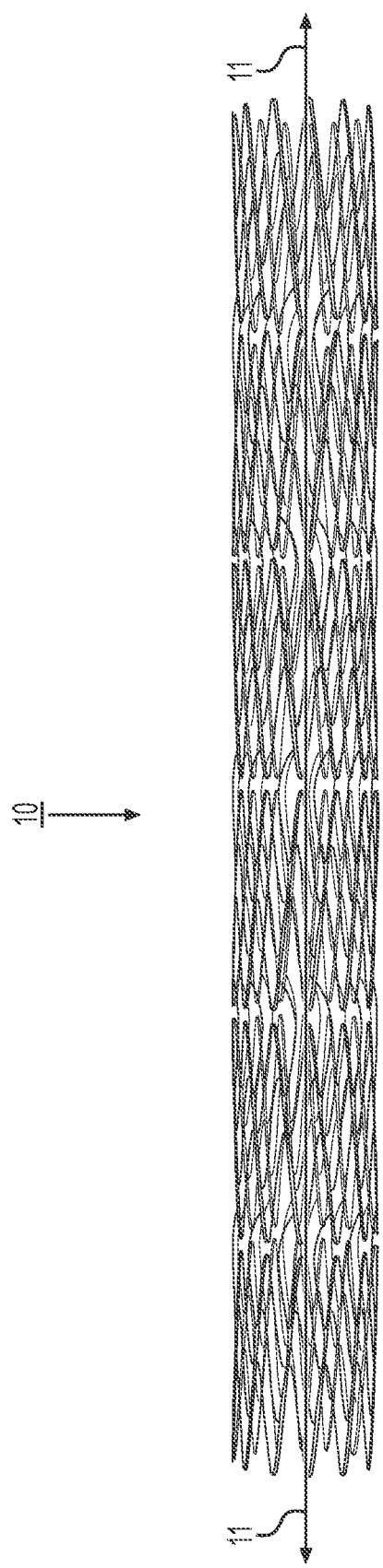
FIG. 4 shows a perspective view of a stent according to one embodiment.

FIG. 4 shows a perspective view of a stent 10 according to one embodiment. The stent 10 has a generally cylindrical form along its longitudinal axis 11 (also referred to herein as the "long axis"), formed by adjacently connected, closed circumferential portions (also referred to herein as "circumferential rings") that connect such that they extend serially along the length of the stent 10. As will be shown in further detail in FIGS. 5-8, a circumferential portion is comprised of a plurality of main struts connected by flexible connector struts.

Figure 5:
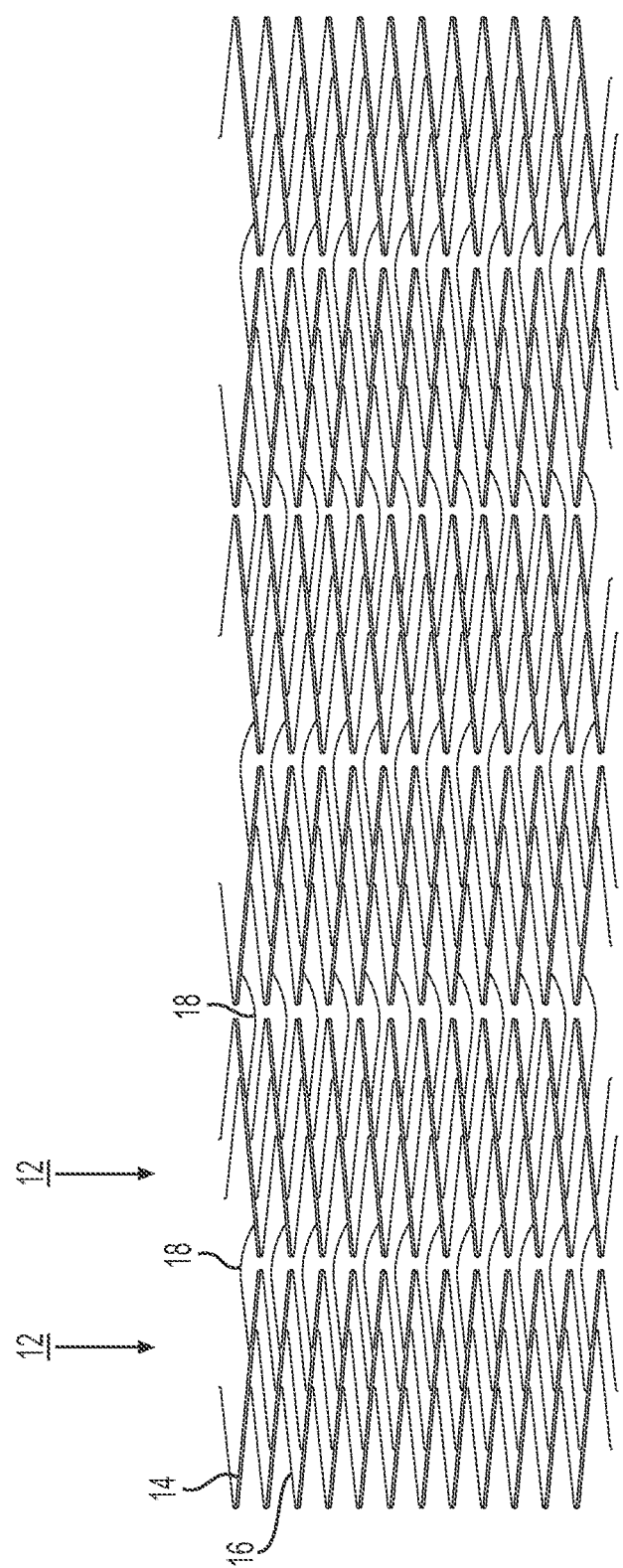
FIG. 5 shows an enlarged view of the stent of FIG. 4, opened up and laid flat.
Figure 6:
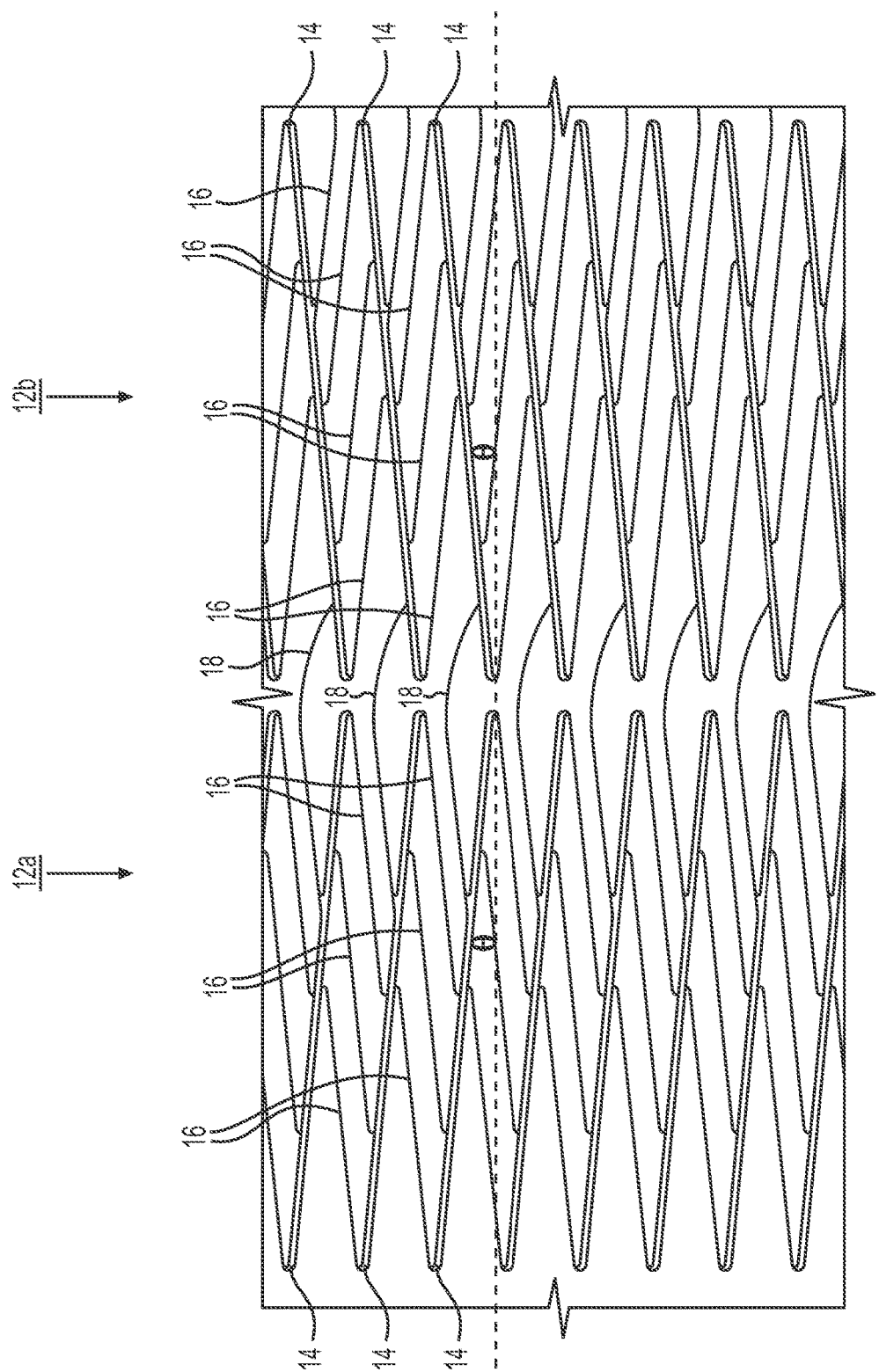
FIG. 6 shows an enlarged side view of two adjacent and connected strip portions from FIG. 5.
Figure 7:
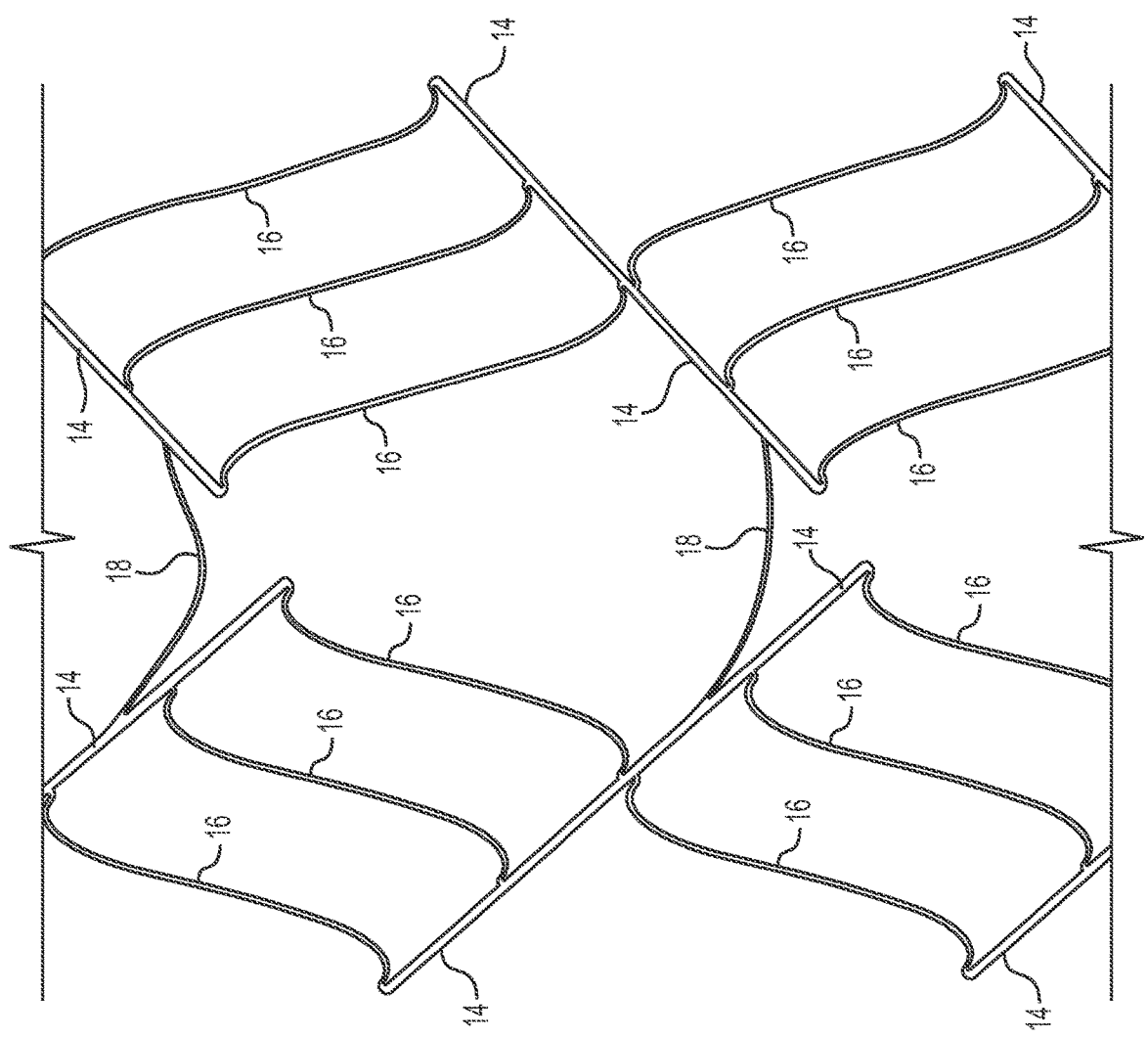
FIG. 7 shows an enlarged perspective view of adjacent and connected strip portions from the stent shown in FIG. 4.

In the illustrations of FIGS. 5 and 6, the stent 10 is opened up and laid flat such that adjacent strips 12 are shown. Structural features of the cylindrical stent shown in FIG. 4 are depicted by a view of the stent 10 in a cut-open and laid flat state. When connected at opposite ends, each strip 12 forms a closed, circumferential portion (circumferential ring) that extends circumferentially around the long axis 11 of the stent 10. For example, circumferential portions that together form the stent 10 can be formed by welding together opposite ends of the strips 12.

As shown in FIGS. 5 and 6, each of the plurality of adjacently connected strips 12 includes a plurality of main struts 14. Each respective main strut 14 is connected to a next respective main strut 14 by a plurality of flexible first connecting struts 16. Edges of each strip 12 are defined by opposing ends of the main struts 14, and each main strut 14 is substantially straight. Second connector struts 18 connect main struts 14 of one strip 12 to main struts 14 of a next adjacent strip 12 along the length of the stent 10. As particularly shown in FIG. 6, each second connector strut 18 connects a main strut 14 of one strip 12 to a main strut 14 of the adjacent strip 12 by extending between the main struts 14.

Structural components of the stent 10 are formed from materials that facilitate reduced foreshortening while providing radial stiffness and flexibility. The main struts 14, first connector structs 16, and/or second connector struts 18, may be, for example formed from nitinol, spring steel, stainless steel, or durable polymer.

When the stent 10 is in a compressed state, for example when in a catheter for delivery, the main struts 14 align nearly in parallel with the centerline of the stent, e.g., nearly parallel to the long axis 11. When the stent 10 is deployed and expands into an uncompressed state, the angular orientation of the main struts 14 increases, such that the main struts 14 are each more obliquely oriented to the long axis 11. In an exemplary embodiment, the angle θ of orientation of the main struts 14 when the stent 10 is expanded in the unconstrained state is between 10 and 50 degrees from the long axis 11, which can be between 5 and 40 degrees when deployed into the patient's lumen. In some embodiments, the range of strut angles is between 15 and 30 degrees from the long axis in the unconstrainted state, which can be between 10 and 25 degrees when deployed into the lumen. In some embodiments, the change in angular orientation corresponds to rotation of the main struts 14 relative to the first connecting struts 16 when expanding from a compressed or otherwise constrained state.

As shown, each main strut 14 of each strip 12 has an oblique orientation relative to the long axis 11 of the stent 10 that is the same oblique orientation of the other main struts 14. It should be appreciated that the angle of orientation of one or more main struts may be different than that of others, either within the same strip or different strips of the stent, in order to provide desired expansion or compression performance of the stent. The second connector struts 18 are also oriented obliquely to the long axis of the stent 10, but at an angular orientation that is generally opposite the oblique orientation of the main struts 14. The second connector struts 18 having an opposite angle, with respect to the long axis of the stent 10, facilitates the angular change in the main struts 14 to increase the length of the second connector struts 18, thus minimizing the foreshortening of the entire stent.

In the exemplary embodiment of the stent 10 shown in FIGS. 4-6, and as can be particularly seen in closer detail in FIG. 6, the angular orientation of each of the main struts 14 of one strip 12 is generally opposite the angular orientation of each of the main struts 14 of an adjacent strip. For example, the main struts 14 of the left strip 12a shown in in FIG. 6 have an angular orientation that is different than and generally opposite the angular orientation of the main struts 14 of the right strip 12b. When viewed along the length of the stent 10 (along the long axis 11), it can be seen that each strip 12 has its main struts 14 oriented oppositely in this manner from one strip 12 to another. That is, the angular orientation of the main struts 14 alternates from one strip to another along the length of the stent 10. In this way, it can be considered that the angular orientation of one closed circumferential portion is opposite to the angular orientation of the next adjacent closed circumferential portion along the length of the stent 10. This alternating arrangement, with opposing orientations facilitates the stent 10 being accurately placed in a manner that minimizes the foreshortening of the stent 10 during deployment.

The main struts 14 are wider and longer than the first connector struts 16. In an exemplary embodiment, the main struts 14 are each at least twice as wide as the first connector struts 16. For example, the main struts may each be 0.03 inches wide, whereas the first connector struts may be 0.01 inches wide. The width of a strut as described herein is generally perpendicular to the strut radial direction. The length of a strut as described herein is generally the distance along the longitudinal axis of the strut between its opposite ends. The length of the first connector struts 16 can be 30%, 50%, or 70% of the length of the main struts 14. As can be particularly seen in the perspective view of FIG. 7, the thinner, flexible first connector struts 16 connect main struts 14 together at locations from between an end and approximately the middle of one main strut 14 (on one side of the main strut, for example the right side) to approximately the middle and other respective end (other side, for example the left side) of the next main strut 14, and this pattern is repeated around the circumference.

Each second connector strut 18 connects a main strut 14 of one strip 12 to a main strut 14 of the adjacent strip 12 by extending between the main struts 14. In particular, the second connector struts 18 connect from a location at approximately the middle of one main strut 14 to a location of an adjacent main strut 14 that is more proximate to an end of that adjacent main strut. This offset facilitates nesting together of adjacent portions formed by the main struts and first connector struts when the stent is compressed or under bending.

In the exemplary embodiment shown in FIGS. 4-7, the second connector struts 18 each have a curved form depicted generally as an arc shape. During expansion, the curved connector struts 18 straighten out and lengthen to compensate for the main struts 14 shifting in their angular orientation from being generally aligned with the long axis 11 of the stent 10 to being obliquely oriented, to thereby provide for minimal or zero foreshortening of the stent 10. As can be particularly seen in FIG. 5, some pairs of adjacent strips 12 are connected by second connector struts 18 that form a curve generally facing upwards, whereas other pairs of adjacent strips 12 are connected by second connector struts 18 with a curve shape that generally faces downwards. In embodiments in which the curve of the second connector struts 18 alternate in facing upwards and downwards from one adjacent strip 12 to the next, this arrangement can allow for the stent 10 to ratchet along its length, with each adjacent strip 12 along the length rotating in a different direction. Although in the exemplary embodiment shown in FIGS. 4-7 each main strut 14 of one strip 12 is connected by a second connector strut 18 to an adjacent main strut 14 of an adjacent strip 12, the configurations are not limited to having a 1-1 correspondence. In some embodiments (not shown), every other set, or every third set, of adjacent main struts, for instance, may be connected by a second connector strut.

Figure 8:
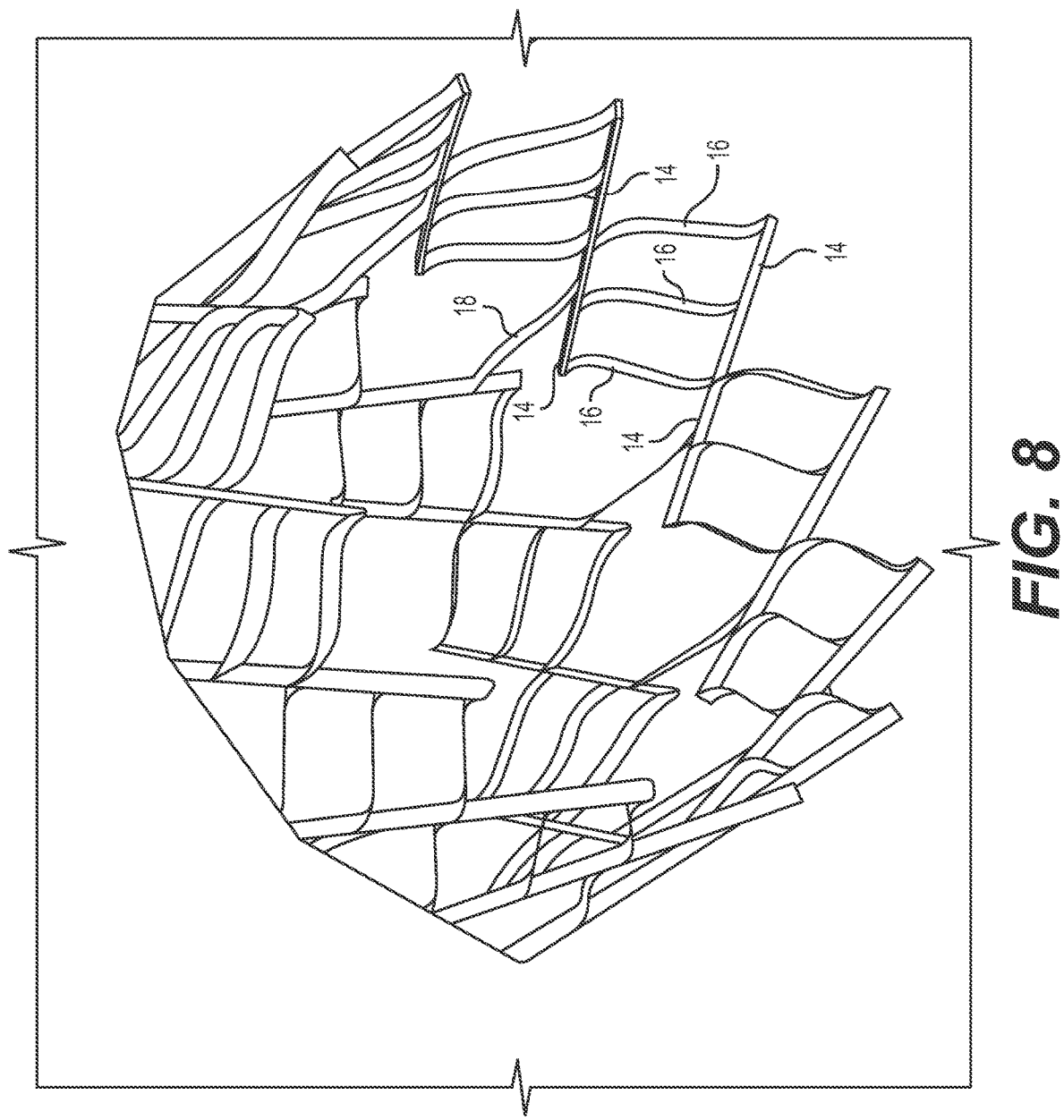
FIG. 8 shows a stent comprised of two connected, adjacent circumferential rings, with each of the rings being formed by respective pluralities of main struts and flexible first connector struts.

FIG. 8 shows a perspective view of a stent formed by two adjacent and connected closed circumferential portions (circumferential rings), each formed by respective pluralities of main struts 14 and flexible first connector struts 16 as described above with respect to FIGS. 4-7. The circumferential rings are connected by second connector struts 18 as described above with respect to FIGS. 4-7.

Figure 9:
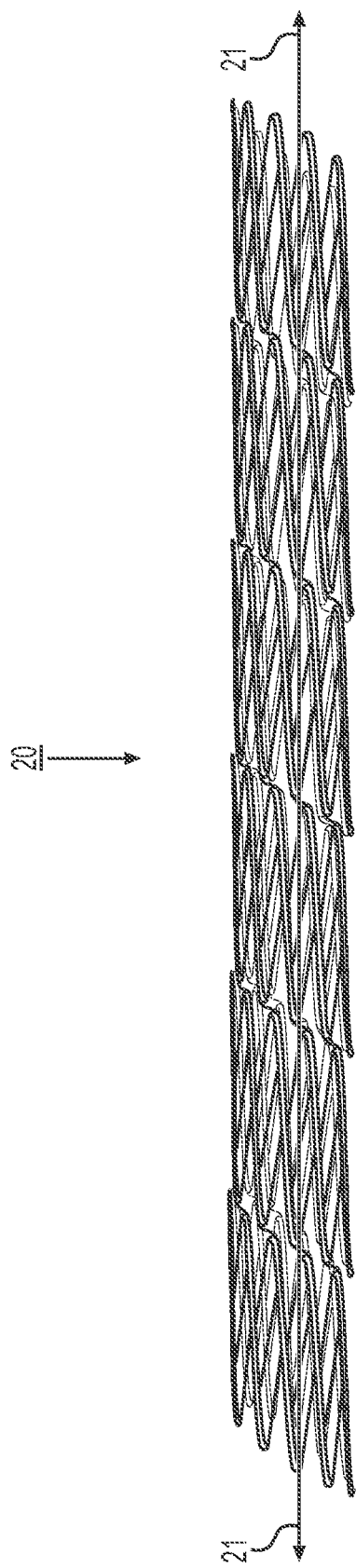
FIG. 9 shows a perspective view of a stent according to another embodiment.
Figure 10:
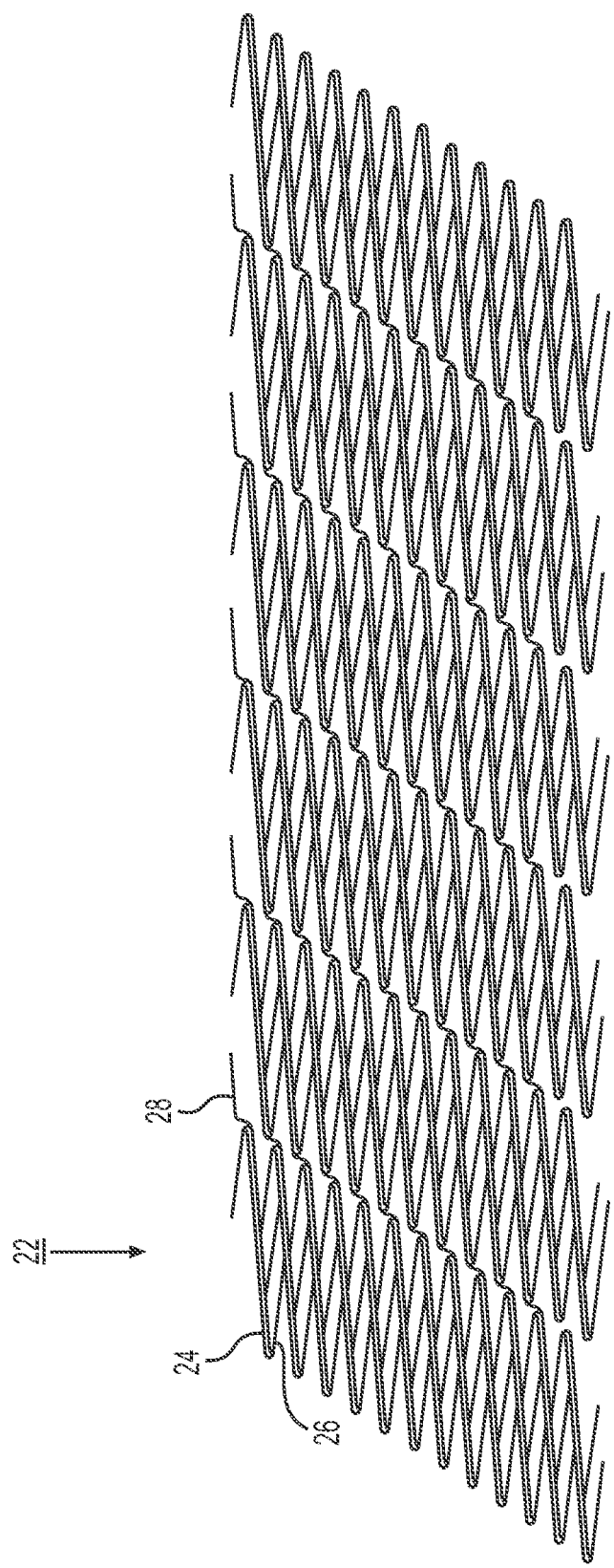
FIG. 10 shows an enlarged view of the stent of FIG. 9, opened up and laid flat.
Figure 11:
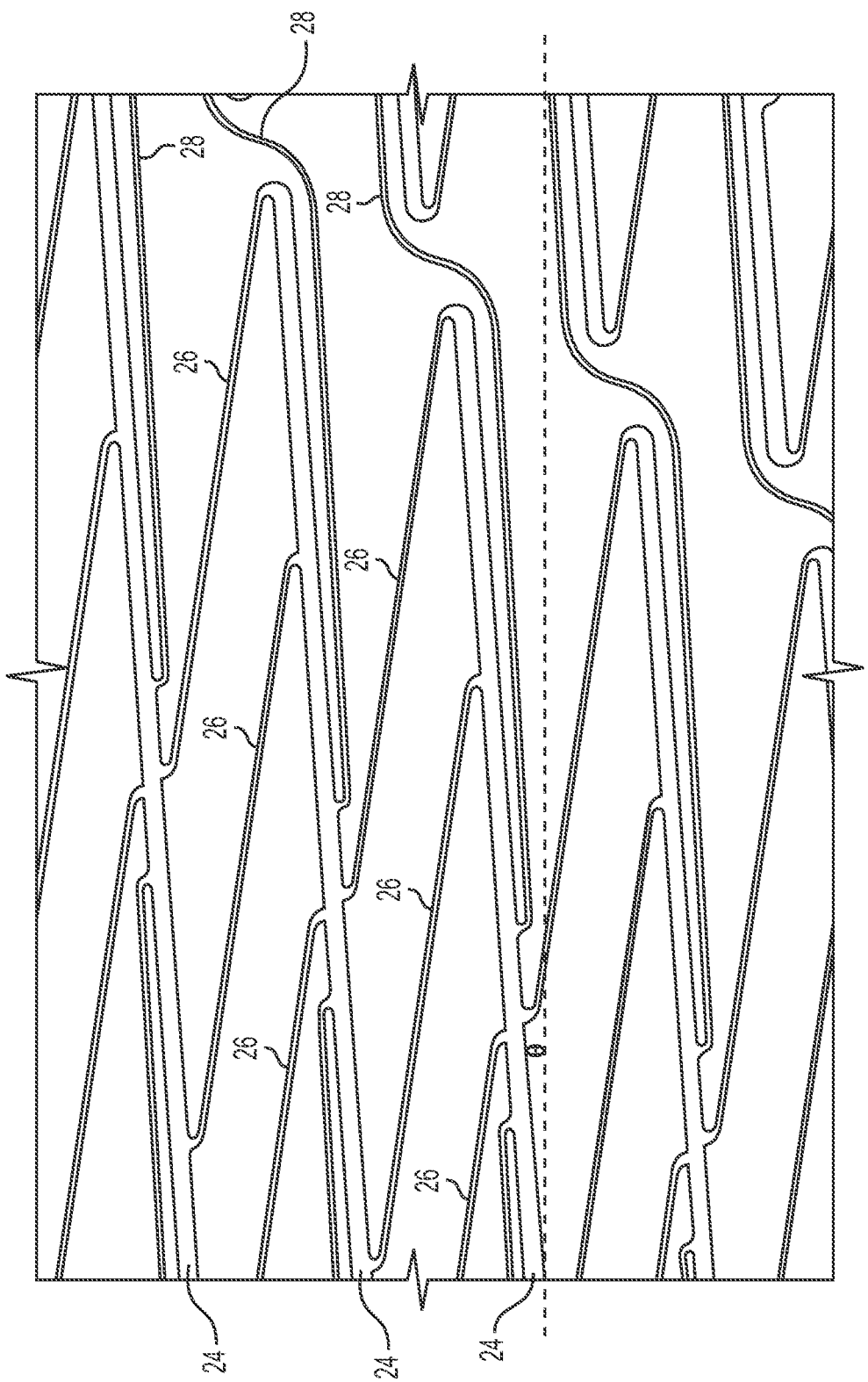
FIG. 11 shows an enlarged, side view of certain connected structures of the stent of FIG. 9 comprised of main struts, first connector struts, and second connector struts.

FIG. 9 shows a perspective view of a stent 20 according to another embodiment. The stent 20 is comprised of portions with main struts, first connector struts, and second connector struts that are connected to form a continuous single strip structure that extends helically and circumferentially around the long axis 21. In the illustrations of FIGS. 10 and 11, the stent 20 is opened up and laid flat such that the strip 22 is shown with cut ends (thus formed of several strips or strip fragments). Structural features of the generally cylindrical-shaped stent 22 shown in FIG. 9 are thereby depicted by a view of the stent 20 in a cut-open and laid flat state. When connected at opposite ends as depicted in FIG. 10, the strips 22 form the helically oriented circumferential arrangement shown in FIG. 9. The connected strips may thereby be considered a continuous helical strip that extends helically around the long axis of the stent.

The strip 22 as shown in the laid-flat view of FIG. 10 includes a plurality of main struts 24 connected by a plurality of flexible, first connector struts 26. Expressed in terms of the axis running from one end of the fragment of strip 22 to the other end (e.g., top to bottom of a strip as shown in FIG. 10), each main strut 24 of the fragment of strip 22 connects to a next main strut 24 along this axis via a plurality of respective first connector struts 26 between them. Each of the main struts 24 is substantially straight along its length. As can be particularly seen in the perspective view of FIG. 12, the first connector struts 26 connect main struts 24 together at locations from between an end and approximately the middle of one main strut 24 to approximately the middle and an end of the next main strut 24.

Figure 12:
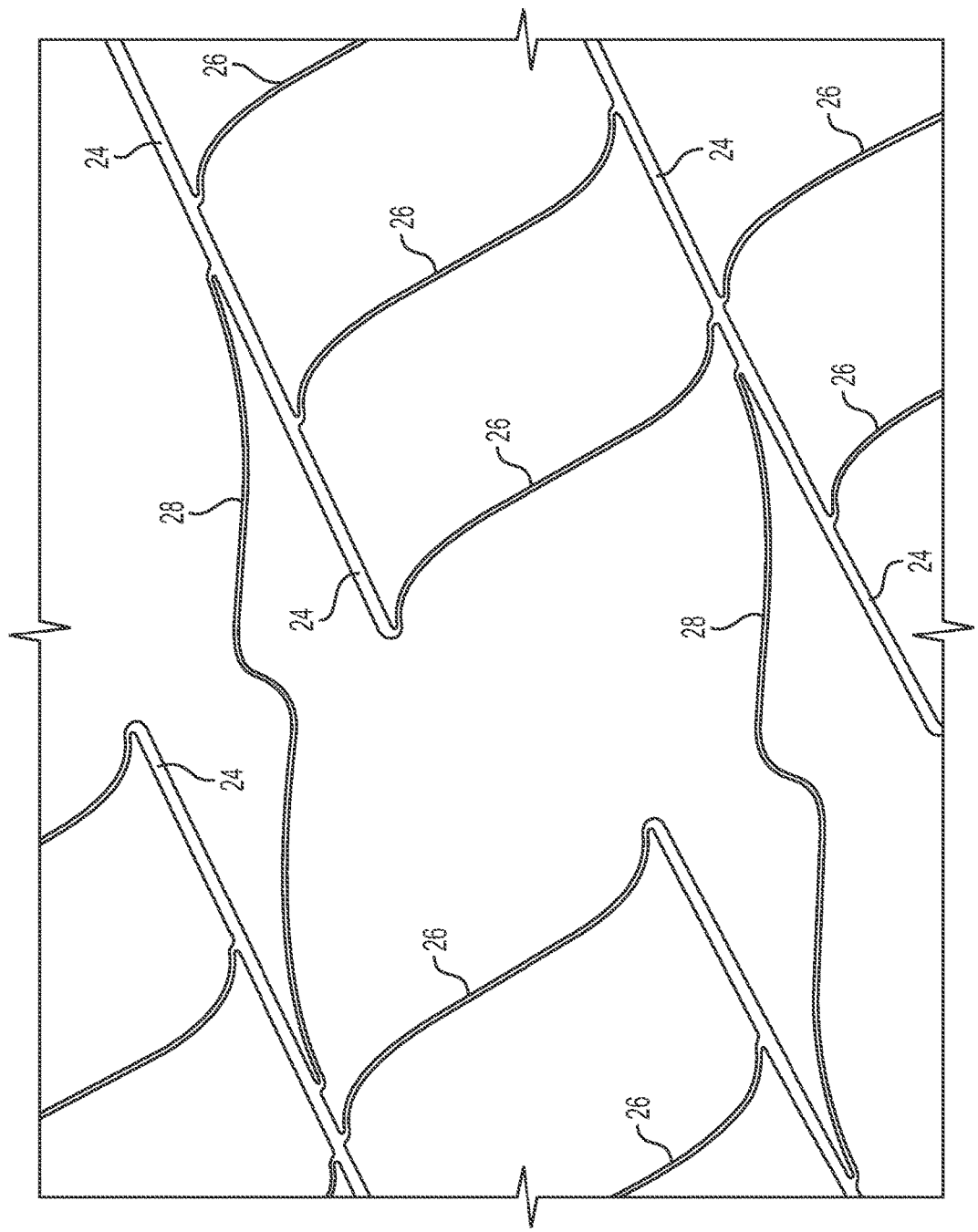
FIG. 12 shows an enlarged perspective view of certain structures of the stent of FIG. 9, with S-shaped second connector struts connecting sets of main struts and first connector struts to other sets of main struts and first connector struts.

As shown in further detail in the enlarged side view of FIG. 11 and perspective view of FIG. 12, main struts 24 of one strip fragment are connected to adjacent main struts 24 of adjacent fragments of strip 22 by respective second connector struts 28. Each main strut 24 is connected to an adjacent main strut 24 by a respective second connector strut 28 that extends in a direction that is generally aligned with the long axis 21 of the stent 20. In the exemplary embodiment shown, each second connector strut is generally S-shaped, with two opposing curves (bends), which facilitates nesting of the struts and helps to minimize foreshortening.

Structural components of the stent 20 are formed from materials that facilitate reduced foreshortening while providing radial stiffness and flexibility. The main struts 24, first connector structs 26, and/or second connector struts 28, may be, for example formed from nitinol, spring steel, stainless steel, or durable polymer.

As can be seen in detail in the perspective view of FIG. 12, each second connector strut 28 attaches from a location that is proximate the middle of each respective main strut 24 between opposing ends of the main strut 24, to a location proximate the middle along the length of the adjacent main strut 24, to facilitate minimizing of foreshortening. Although in the exemplary embodiment shown in FIGS. 9-12, each main strut 24 of one fragment of strip 22 is connected by a second connector strut 28 to an adjacent main strut 24 of an adjacent fragment of strip 22, the configurations are not limited to having a 1-1 correspondence. In some embodiments (not shown), every other set, or every third set, of adjacent main struts, for instance, may be connected by a second connector strut.

The main struts 24 are wider and longer than the first connector struts 26. In an exemplary embodiment, the main struts 24 are each at least twice as wide as the first connector struts 26. For example, the main struts 24 may each be 0.03 inches wide, whereas the first connector struts 28 may be 0.01 inches wide. The length of the first connector struts 26 can be 30%, 50%, or 70% of the length of the main struts 24.

When the stent 20 is in a compressed state, for example when in a catheter for delivery, the main struts 24 align nearly in parallel with the centerline of the stent, more parallel to the long axis 21. When the stent 20 is deployed and expands into an uncompressed state, the angular orientation of the main struts 24 increases, such that the main struts 24 each become more obliquely oriented to the long axis 21. In an exemplary embodiment, the angle θ of orientation of the main struts 24 is between 10 and 50 degrees from the long axis 21 of the stent 20 when the stent 20 is in the expanded state.

In the embodiment shown, each main strut 24 of each strip 22 has an angle θ of orientation relative to the long axis 21 of the stent 20 that is the same as that of the other main struts 24. It should be appreciated that the angle of orientation of one or more main struts may be different than that of others, either within the same strip or different strips of the stent, in order to provide desired expansion or compression performance of the stent. The second connector struts 28 are also oriented obliquely to the long axis of the stent 20, but at an angular orientation that is generally opposite the oblique orientation of the main struts 24. The second connector struts having an opposite angle, with respect to the long axis of the stent, facilitates the angular change in the main struts to increase the length of the second connector struts, thus minimizing the foreshortening of the entire stent.

To deploy an implantable stent according to embodiments described herein, the stent may be radially compressed/crimped to a smaller diameter for loading onto/into a delivery catheter. The stent may be crimped over a balloon on the inner core of the delivery system which may be later inflated to expand the coiled stent to the desired diameter. The engagement fingers are pre-configured at specific locations to allow discrete incremental expansion of the stent. In some embodiments, the stent can be expanded in 0.5 mm increments. In some embodiments, more than one stent may be joined together. For example, the ultimate length of the stent can be controlled by joining any desired number of individual adaptive diameter cells via flexible or rigid bridge members.

Implantable stents such as those described above may advantageously provide an adaptive diameter and/or flexibility to conform the dynamic movement of peripheral veins in leg/pelvis thereby facilitating treatment of both iliac vein compression syndrome and ilio-femoral venous outflow obstructions.

It may be desirable to have a stent that will conform to the existing path of a vein instead of a straightening out of the vessel by the stent. It may also be desirable to have a high radial stiffness of the stent to resist collapse of the stent under crushing load and to maximize the resultant diameter of the treated vessel at the location of the stent deployment. With most stent constructions there is a direct relationship between radial stiffness and axial stiffness.

Common commercially available balloon expandable stents experience a dramatic change in length as a balloon is used to expand the stent within the vessel. Common commercially available self-expanding stents experience a change in length less dramatic, but still substantial, which increases with increasing stent length. Change in length between the configuration within the delivery system and when deployed in the vessel causes difficulty in placing/landing the stent precisely at the target location. When the stent is deployed in its crimped configuration and expanded, the shortening in length causes the stent target deployment location to have to offset from the target dwell location. The magnitude of this effect is not controllable or easily anticipated as it is dependent on the luminal cross-section along the length of the target dwell location (which is frequently and unexpectedly influenced by residual stenosis, irregular shape due to external objects, and/or forces, etc.). For target lesions leading up to the junction of the left and right iliac into the IVC, this causes difficulty in placing the stent to dwell completely within the iliac along its total length up to the junction to the inferior vena cava without crossing into the inferior vena cava.

In some embodiments a venous stent with high radial force, no impactful foreshortening along multiple lengths, and high flexibility/vessel conformity is provided. Minimization of foreshortening allows the stent advantageously accurate and predictable deployment. And, high flexibility maximizes the fatigue life of the stent under bending. Of course, it will be understood that the stent may find applications in the arterial system as well.

Embodiments disclosed herein can be used for both balloon expandable and self-expanding stent designs. The stent designs can be used for all stent interventions, including coronary, peripheral, carotid, neuro, biliary and, especially, venous applications. Additionally, this could be beneficial for stent grafts, percutaneous valves, etc.

Currently available implants are typically loaded and retained onto a delivery system in a crimped configuration and then navigated and deployed in the desired anatomical location where they expand to the implanted configuration. The final implanted configuration can be achieved through mechanical expansion/actuation (e.g., balloon-expandable) or self-expansion (e.g., Nitinol). Self-expanding implants are manufactured from super elastic or shape memory alloy materials. Accurate and precise deployment of a self-expanding implant can be challenging due to a number of inherent design attributes associated with self-expanding implants. The implant may jump/advance from the distal end of the delivery system during deployment due to the stored elastic energy of the material. Additionally, the implant may foreshorten during deployment due to the change in the implant diameter from the crimped configuration to the expanded configuration. Finally, physiological and anatomical configurations, such a placement at or near bifurcations of body lumens, can affect accurate placement of implants. Once the implant is placed within the body lumen there is potential for uneven expansion or lack of circumferential implant apposition to the body lumen which can result in movement, migration or in certain severe cases implant embolization.

In some embodiments, a self-expanding implant designed with sufficient radial force to resist constant compression of the body lumen while providing optimal fatigue resistance, accurate placement, and in-vivo anchoring to prevent is provided. Additionally, various methods for deployment and implantation for treating iliac vein compression syndrome and venous insufficiency disease are provided.

In some embodiments, the implant comprises a purposely designed stent intended to focally treat iliac vein compression (May-Thurner Syndrome). The implant may be relatively short in length (~40 mm) and may be manufactured from self-expending Nitinol with integrated anchor features to aid in accurate placement and to mitigate migration following implantation. The implant and delivery system are designed for precise deployment and placement at the bifurcation of the inferior vena cava into the right and left common iliac veins.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Features described in conjunction with a particular aspect, embodiment or example of the invention are to be understood to be applicable to any other aspect, embodiment or example described herein unless incompatible therewith. All of the features disclosed in this specification (including the accompanying claims, abstract, and drawings) and/or all of the steps of any method or process so disclosed, may be combined in any combination, except combinations where at least some of such features and/or steps are mutually exclusive.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A stent comprising:
    at least one strip including a plurality of main struts and a plurality of first connector struts,
        wherein the main struts are obliquely oriented to a longitudinal axis of the stent, and wherein the at least one strip extends circumferentially around the longitudinal axis of the stent,
        wherein the first connector struts extend between and connect circumferentially adjacent pairs of the main struts and opposing ends of each main strut of the plurality of main struts define respective opposing edges of the at least one strip,
        wherein at least one of the first connector struts connects each circumferentially adjacent pair of the main struts from one of the opposing ends of a first main strut of the circumferentially adjacent pair to a location between the opposing ends of a second main strut of the circumferentially adjacent pair; and
    a plurality of second connector struts, wherein ends of the second connector struts are connected to the main struts between the opposing ends of the main struts so as to reduce foreshortening of the stent during expansion; and
    wherein at least another one of the first connector struts connects each circumferentially adjacent pair of the main struts from a location between the opposing ends of the first main strut to a location between the opposing ends of the second main strut.

2. The stent of claim 1, wherein the first main strut and the second main strut have the same oblique orientation relative to the longitudinal axis of the stent.

3. The stent of claim 1, wherein the first connector struts are obliquely oriented to the longitudinal axis of the stent.

4. The stent of claim 3, wherein the oblique orientation of the first connector struts is opposite the oblique orientation of the main struts.

5. The stent of claim 1, wherein each of the main struts is generally straight between its ends.

6. The stent of claim 1, wherein each of the first connector struts is generally straight between its ends.

* * * * *